United States Patent
Liao et al.

(10) Patent No.: US 8,552,873 B2
(45) Date of Patent: Oct. 8, 2013

(54) METHOD AND SYSTEM FOR DETECTING A DRIVING STATE OF A DRIVER IN A VEHICLE

(75) Inventors: Yu-Sheng Liao, Lugong (TW);
Chia-Tseng Chen, Lugong (TW);
Yu-Sung Chen, Lugong (TW)

(73) Assignee: Automotive Research & Testing Center, Lugong (TW)

( * ) Notice: Subject to any disclaimer, the term of this patent is extended or adjusted under 35 U.S.C. 154(b) by 303 days.

(21) Appl. No.: 12/979,939

(22) Filed: Dec. 28, 2010

(65) Prior Publication Data
US 2012/0161954 A1 Jun. 28, 2012

(51) Int. Cl.
*G08B 23/00* (2006.01)
(52) U.S. Cl.
USPC .................. 340/576; 340/573.1; 180/272
(58) Field of Classification Search
None
See application file for complete search history.

(56) References Cited

U.S. PATENT DOCUMENTS 6,661,345 B1 * 12/2003 Bevan et al. .................. 340/575
6,717,518 B1 * 4/2004 Pirim et al. .................. 340/576

FOREIGN PATENT DOCUMENTS

CN 1495658 A 5/2004
TW 201003570 A 1/2010

OTHER PUBLICATIONS

Search Report of Taiwan Patent Application No. 099146899 mailed Feb. 22, 2013, 1 page.

* cited by examiner

*Primary Examiner* — Mohammad Ghayour
*Assistant Examiner* — Brian Wilson
(74) *Attorney, Agent, or Firm* — Lando & Anastasi, LLP

(57) ABSTRACT

In a method and system for detecting a driving state of a driver in a vehicle, a face recognition standard corresponding to an environmental condition within the vehicle is established based on a series of image frames generated by capturing consecutively images of the driver upon movement of the vehicle. Upon detection of a variance in the environmental condition during movement of vehicle, the face recognition standard is updated with a corrected face recognition standard corresponding to the environmental condition with the variance. It is determined based on the corrected face recognition standard and the image frames whether the driving state of the driver is a dangerous state, where the driver's face does not face a front windshield of the vehicle or where the driver's face faces the front windshield of the vehicle but one of the driver's eyes is closed.

10 Claims, 2 Drawing Sheets

METHOD AND SYSTEM FOR DETECTING A DRIVING STATE OF A DRIVER IN A VEHICLE

BACKGROUND OF THE INVENTION

1. Field of the Invention

The invention relates to a method and system for detecting a driving state of a driver in a vehicle.

2. Description of the Related Art

In a conventional detecting system for a driver in a vehicle using facial feature recognition, a predetermined face recognition threshold value is used as a fixed face recognition standard to determine whether the driver is in suitable condition for driving. The conventional detecting system determines, based on the fixed face recognition standard, whether the driver's face faces a front windshield of the vehicle and whether the driver's eyes are closed. However, for different drivers, and various environmental conditions within the vehicle, such as various illuminations and various light sources, the conventional detecting system cannot ensure correct detection result using the fixed face recognition standard.

SUMMARY OF THE INVENTION

Therefore, an object of the present invention is to provide a method and system for detecting a driving state of a driver in a vehicle that can overcome the aforesaid drawback of the prior art.

According to one aspect of the present invention, there is provided a method of detecting a driving state of a driver in a vehicle. The method comprises the steps of:

a) capturing consecutively images of the driver in the vehicle to generate a series of image frames;

b) establishing a face recognition standard corresponding to an environmental condition within the vehicle based on the image frames generated in step a) upon movement of the vehicle;

c) during movement of the vehicle, determining whether there is a variance in the environmental condition;

d) upon determining that there is a variance in the environmental condition, updating the face recognition standard with a corrected face recognition standard that corresponds to the environmental condition with the variance and that is generated based on the image frames generated in step a) under the environmental condition with the variance; and e) determining, based on the corrected face recognition standard, and the image frames generated after the corrected face recognition standard is generated, whether the driving state of the driver is a dangerous state, where the driver's face does not face a front windshield of the vehicle or where the driver's face faces the front windshield of the vehicle but at least one of the driver's eyes is closed.

According to another aspect of the present invention, there is provided a system for detecting a driving state of a driver in a vehicle. The system comprises:

an image capturing unit for capturing consecutively images of the driver in the vehicle to generate a series of image frames;

a processing unit coupled to the image capturing unit, receiving the image frames from the image capturing unit, and operable to process the image frames to establish a face recognition standard corresponding to an environmental condition within the vehicle upon movement of the vehicle; and a detecting unit coupled to the processing unit for detecting the environmental condition during movement of the vehicle, the detecting unit outputting a trigger signal to the processing unit upon detecting a variance in the environment condition.

The processing unit generates a corrected face recognition standard corresponding to the environmental condition with the variance based on the image frames from the image capturing unit upon receipt of the trigger signal from the detecting unit, updates the face recognition standard with the corrected face recognition standard, and determines, based on the corrected face recognition standard and the image frames from the image capturing unit, whether the driving state of the driver is a dangerous state, where the driver's face does not face a front windshield of the vehicle or where the driver's face faces the front windshield of the vehicle but at least one driver's eye is closed.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
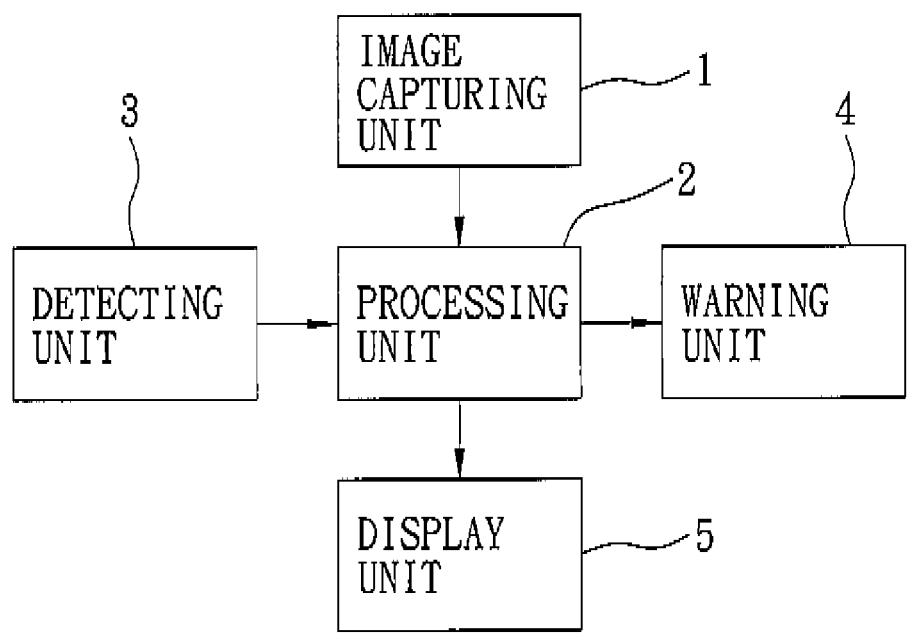
FIG. 1 is a schematic circuit block diagram illustrating the preferred embodiment of a system for detecting a driving state of a driver in a vehicle according to the present invention.

Referring to FIG. 1, the preferred embodiment of a system for detecting a driving state of a driver in a vehicle according to the present invention is shown to include an image capturing unit 1, a processing unit 2, a detecting unit 3, a warning unit 4, and a display unit 5.

The image capturing unit 1 captures consecutively images of the driver in the vehicle to generate a series of image frames when the vehicle is started. In this embodiment, the image capturing unit 1 includes a CCD/CMOS video camera.

The processing unit 2 is coupled to the image capturing unit 1, and receives the image frames from the image capturing unit 1. The processing unit 2 is operable to process the image frames to establish a face recognition standard corresponding to an environmental condition within the vehicle upon movement of the vehicle. The face recognition standard is associated with a facial feature of the driver that corresponds to a portion of the driver's face with at least one of eyes, nose and mouth, and a predetermined open-eye image sample. In this embodiment, the facial feature of the driver corresponds to a portion of the driver's face with eyes, nose and mouth. The face recognition standard includes a first threshold value and a second threshold value. The first threshold value is obtained from face detection scores of sub-image frames of a predetermined number of the image frames from the image capturing unit 1 corresponding to the portion of the driver's face generated using known face detection techniques. The second threshold value is obtained from a correlation coefficient between each of sub-image frames of the predetermined number of the image frames corresponding to one driver's eye, and the predetermined open-eye image sample. For example, the first threshold value can be computed by subtracting a product of a variable parameter (n) and a standard difference for the face detection scores from an average value of the face detection scores, and the second threshold value can be computed by subtracting a product of a variable parameter (n') and a standard difference for the correlation coefficients from an average value of the correlation coefficients, wherein n and n' are adjusted as requirements of the system.

The detecting unit 3 is coupled to the processing unit 2 for detecting the environmental condition during movement of the vehicle. The detecting unit 3 outputs a trigger signal to the processing unit 2 upon detecting a variance in the environmental condition. The variance of the environment condition includes variation in illumination within the vehicle and variation in an orientation of an external light source relative to the driver's face. In this embodiment, the detecting unit may determine whether there is a variation in illumination within the vehicle in accordance with transformation for operation of headlights of the vehicle. Alternatively, the detecting unit 3 includes a plurality of illumination sensors composed of photosensitive devices, such as photosensitive resistors, that are arranged to sense illumination within the vehicle. As a result, the detecting unit 3 can determine whether there is a variation in illumination within the vehicle or the orientation of the external light source in accordance with variations in currents flowing respectively through the photosensitive devices. In addition, when the driver turns the vehicle by rotating a steering wheel of the vehicle, there may be a variation in an orientation of a fixed light source, such as sunlight, relative to the driver's face. Thus, the detecting unit 3 may determine the variation in the external light source in accordance with rotation of the steering wheel.

The processing unit 2 is operable to generate a corrected face recognition standard corresponding to the environmental condition with the variance based on the image frames, which are generated by the image capturing unit 1 under the environmental condition with the variance, upon receipt of the trigger signal from the detecting unit 3. The corrected face recognition standard includes first and second threshold values that are generated in the same manner as those for the face recognition standard. Then, the processing unit 2 updates the face recognition standard with the corrected face recognition standard. Thereafter, the processing unit 3 determines whether the driving state of the driver is a dangerous state based on the corrected face recognition standard, and the image frames from the image capturing unit 1. When the driving state of the driver is the dangerous state, the driver's face does not face a front windshield of the vehicle or the driver's face faces the front windshield of the vehicle but at least one of the driver's eyes is closed.

The processing unit 2 is operable to generate a face detection result of a number of the image frames from the image capturing unit 1 after generation of the corrected face recognition standard and to determine whether the face detection result matches the corrected face recognition standard. When the processing unit determines that the face detection result does not match the corrected face recognition standard, the driving state of the driver is the dangerous state. In this embodiment, the face detection result includes a first detection value and a second detection value. The first detection value is an average value of the face detection scores of sub-image frame of the number of the image frames corresponding to the portion of the driver's face. The second detection value is an average value of correlation coefficients between sub-image frames of the number of the image frames corresponding to the driver's eye, and the predetermined open-eye image sample. Therefore, when the first detection value is less than the first threshold value of the corrected face recognition standard, the processing unit 2 determines that the face detection result does not match the corrected face recognition standard. In this case, the dangerous state indicates that the driver's face does not face the front windshield of the vehicle. In addition, when the first detection value is greater than the first threshold value of the corrected face recognition standard but the second detection value is less than the second threshold value of the corrected face recognition standard, the processing unit 2 determines that the face detection result does not match the corrected face recognition standard. In this case, the dangerous state indicates that the driver's face faces the front windshield of the vehicle but one of the driver's eyes is closed.

The processing unit 2 is operable to generate a warning output upon determining that the driving state of the driver is the dangerous state.

The warning unit 4 is coupled to the processing unit 2 for receiving the reproducing the warning output from the processing unit 2. The warning unit 4 can include at least one of a buzzer or an LED.

The display unit 5 is coupled to the processing unit for displaying the images captured by the image capturing unit 1.

Figure 2:
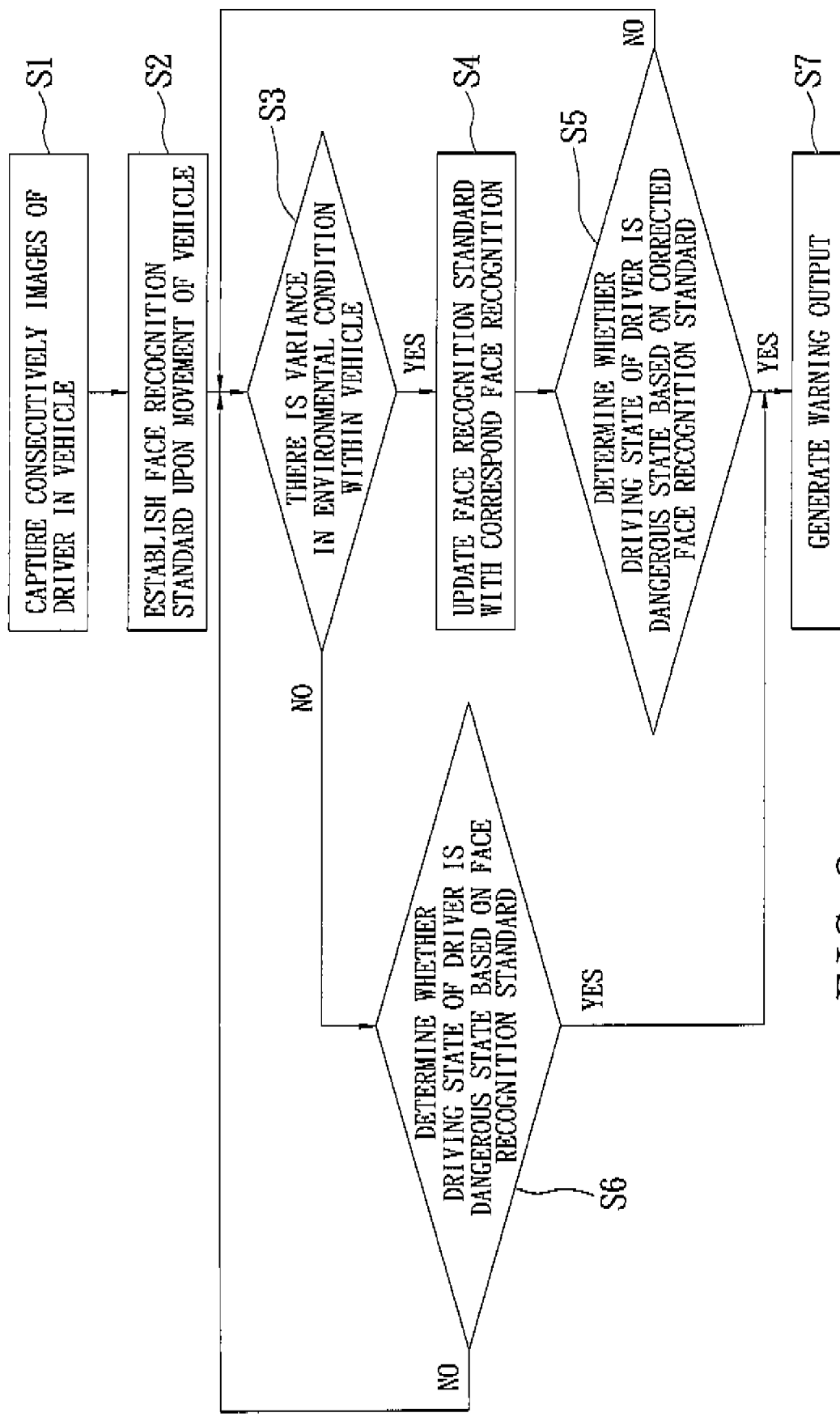
FIG. 2 is a flow chart of a method of detecting the driving state of a driver in a vehicle performed by the preferred embodiment.

FIG. 2 illustrates a flow chart of a method of detecting a driving state of a driver in a vehicle performed by the preferred embodiment.

In step S1, the image capturing unit 1 captures consecutively images of the driver in the vehicle to generating a series of image frames when the vehicle is started.

In step S2, upon movement of the vehicle, the processing unit 2 establishes a face recognition standard corresponding to an environmental condition within the vehicle based on the image frames from the image capturing unit 1.

In step S3, the detecting unit determines whether there is a variance in the environmental condition. If affirmative, the flow proceeds to step S4. Otherwise, the flow goes to step S6.

In step S4, the processing unit 2 is configured to generate a corrected face recognition standard corresponding to the environmental condition with the variance, and updates the face recognition standard with the corrected face recognition standard.

In step S5, the processing unit 2 is configured to determine whether the driving state of the driver is a dangerous state based on the corrected face recognition standard. If affirmative, the flow processed to step 37. Otherwise, the flow goes back to step S3.

In step S6, the processing unit 2 is configured to determine whether the driving state of the driver is the dangerous state based on the face recognition standard. If affirmative, the flow goes to step S7. Otherwise, the flow goes back to step S3.

In step S7, the processing unit 2 is configured to generate a warning output that is reproduced by the warning unit 4.

In sum, the face recognition standard can be established for different drivers, and the corrected face recognition standard can be generated for various environmental conditions within the vehicle. Therefore, the system of the present invention can provide enhanced detecting effect and has superior applicability as compared to the aforesaid conventional detecting system.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method of detecting a driving state of a driver in a vehicle, comprising the steps of:
   a) capturing consecutively images of the driver in the vehicle to generate a series of image frames;
   b) establishing a face recognition standard corresponding to an environmental condition within the vehicle based on the image frames generated in step a) upon movement of the vehicle;
   c) during movement of the vehicle, determining whether there is a variance in the environmental condition;
   d) upon determining that there is a variance in the environmental condition, updating the face recognition standard with a corrected face recognition standard that corresponds to the environmental condition with the variance and that is generated based on the image frames generated in step a) under the environmental condition with the variance; and
   e) determining, based on the corrected face recognition standard, and the image frames generated after the corrected face recognition standard is generated, whether the driving state of the driver is a dangerous state, where the driver's face does not face a front windshield of the vehicle or where the driver's face faces the front windshield of the vehicle but at least one of the driver's eyes is closed;
   wherein step e) further includes the sub-steps of:
   e-1) generating a face detection result of a number of the image frames generated in step a) upon generation the corrected face recognition standard; and
   e-2) determining whether the face detection result generated in sub-step e-1) matches the corrected face recognition standard, the driving state of the driver being in the dangerous state upon determining that the face detection result does not match the corrected face recognition standard;
   wherein each of the face recognition standard and the corrected face recognition standard is associated with a facial feature of the driver that corresponds a portion of the driver's face with at least one of eyes, nose and mouth; and
   wherein:
   each of the face recognition standard and the corrected face recognition standard includes a first threshold value that is obtained from face detection scores of sub-image frames of the image frames corresponding to the portion of the driver's face;
   the face detection result includes a first detection value that is an average value of face detection scores of sub-image frames of the number of the image frames corresponding to the portion of the driver's face; and
   when the first detection value is less than the first threshold value of the corrected face recognition standard, the face detection result does not match the corrected face recognition threshold standard, and the dangerous state indicates that the driver's face does not face the front windshield of the vehicle.

2. The method as claimed in claim 1, further comprising the step of:
   f) upon determining that the driving state of the drive is the dangerous state in step e), generating a warning output.

3. The method as claimed in claim 1, wherein the variance of the environmental condition includes at least one of variation in illumination within the vehicle, and variation in an orientation of an external light source relative to the driver's face.

4. The method as claimed in claim 1, wherein each of the face recognition standard and the corrected face recognition standard is further associated with a predetermined open-eye image sample.

5. The method as claimed in claim 4, wherein:
   each of the face recognition standard and the corrected face recognition standard further includes a second threshold value that is obtained from correlation coefficients between sub-image frames of the image frames corresponding to one driver's eye, and the predetermined open-eye image sample;
   the face detection result further includes a second detection value that is an average value of correlation coefficients between sub-image frames of the number of the image frames corresponding to the driver's eye, and the predetermined open-eye image sample; and
   when the first detection value is greater than the first threshold value of the corrected face recognition standard but the second detection value is less than the second threshold value of the corrected face recognition standard, the face detection result does not match the face recognition standard, and the dangerous state indicates that the driver's face faces the front windshield of the vehicle but the driver's eye is closed.

6. A system for detecting a driving state of a driver of a vehicle, comprising:
   an image capturing unit for capturing consecutively images of the driver in the vehicle to generate a series of image frames;
   a processing unit coupled to said image capturing unit, receiving the image frames from said image capturing unit, and operable to process the image frames to establish a face recognition standard corresponding to an environmental condition within the vehicle upon movement of the vehicle; and
   a detecting unit coupled to said processing unit for detecting the environmental condition during movement of the vehicle, said detecting unit outputting a trigger signal to said processing unit upon detecting a variance in the environmental condition;
   wherein said processing unit
      generates a corrected face recognition standard corresponding to the environmental condition with the variance based on the image frames from said image capturing unit upon receipt of the trigger signal from said detecting unit,
      updates the face recognition standard with the corrected face recognition standard, and
      determines, based on the corrected face recognition standard and the image frames from said image capturing unit, whether the driving state of the driver is a dangerous state, where the driver's face does not face a front windshield of the vehicle or where the driver's face faces the front windshield of the vehicle but at least one of the driver's eyes is closed;
   wherein:
   said processing unit is operable to generate a face detection result of a number of the image frames from said image capturing unit upon generation the corrected face recognition standard and to determine whether the face detection result matches the corrected face recognition standard; and
   when said processing unit determines that the face detection result does not match the corrected face recognition standard, the driving state of the driver is the dangerous state;

wherein each of the face recognition standard and the corrected face recognition standard is associated with a facial feature of the driver that includes a portion of the driver's face with at least one of eyes, nose and mouth; and wherein said processing unit is operable so that:

each of the face recognition standard and the corrected face recognition standard includes a first threshold value that is associated with face detection scores of sub-image frames of the image frames corresponding to the portion of the driver's face;

the face detection result includes a first detection value that is an average value of face detection scores of sub-image frames of the number of the image frames corresponding to the portion of the driver's face; and when the first detection value is less than the first threshold value of the corrected face recognition standard, the face detection result does not match the corrected face recognition standard, and the dangerous state indicates that the driver's face does not face the front windshield of the vehicle.

7. The system as claimed in claim 6, wherein said processing unit is operable to generate a warning output upon determining that the driving state of the driver is the dangerous state, said system further comprising a warning unit coupled to said processing unit for receiving and reproducing the warning output from said processing unit.

8. The system as claimed in claim 6, wherein the variance of the environmental condition includes at least one of variation in illumination within the vehicle, and variation in an orientation of an external light source relative to the driver's face.

9. The system as claimed in claim 6, wherein each of the face recognition standard and the corrected face recognition standard is further associated with a predetermined open-eye image sample.

10. The system as claimed in claim 9, wherein said processing unit is operable so that:

each of the face recognition standard and the corrected face recognition standard further includes a second threshold value that is obtained from correlation coefficients between sub-image frames of the image frames corresponding to one driver's eye, and the predetermined open-eye image sample;

the face detection result further includes a second detection value that is an average value of correlation coefficients between sub-image frames of the number of the image frames corresponding to the driver's eye, and the predetermined open-eye image sample; and when the first detection value is greater than the first threshold value of the corrected face recognition standard but the second detection value is less than the second threshold value of the corrected face recognition standard, the face detection result does not match the face recognition standard, and the dangerous state indicates that the driver's face faces the front windshield of the vehicle but the driver's eye is closed.

\* \* \* \* \*